(12) United States Patent
Teychene et al.

(10) Patent No.: US 12,402,599 B2
(45) Date of Patent: Sep. 2, 2025

(54) GRIPPER FOR MANIPULATING A DEVICE FOR IDENTIFYING AN ANIMAL AND/OR REMOVING TISSUE FROM AN ANIMAL COMPRISING HOLDING MEANS WITH REMOTE ACTUATION

(71) Applicant: ALLFLEX EUROPE SAS, Vitre (FR)

(72) Inventors: Bruno Teychene, Mouzieys-Teulet (FR); Philippe Blanc-Tailleur, Toulouse (FR)

(73) Assignee: ALLFLEX EUROPE SAS, Vitre (FR)

( * ) Notice: Subject to any disclaimer, the term of this patent is extended or adjusted under 35 U.S.C. 154(b) by 978 days.

(21) Appl. No.: 17/282,004

(22) PCT Filed: Oct. 2, 2019

(86) PCT No.: PCT/EP2019/076775
§ 371 (c)(1),
(2) Date: Apr. 1, 2021

(87) PCT Pub. No.: WO2020/070227
PCT Pub. Date: Apr. 9, 2020

(65) Prior Publication Data
US 2021/0345583 A1 Nov. 11, 2021

(30) Foreign Application Priority Data
Oct. 3, 2018 (FR) ........................ 1859184

(51) Int. Cl.
*A01K 11/00* (2006.01)
*A61B 10/02* (2006.01)

(52) U.S. Cl.
CPC .......... *A01K 11/002* (2013.01); *A01K 11/003* (2013.01); *A61B 10/0233* (2013.01);
(Continued)

(58) Field of Classification Search
CPC .. A01K 11/002; A01K 11/003; A01K 11/001; A61B 10/0233; A61B 2503/40; A61B 10/0266; A61B 10/02
See application file for complete search history.

(56) References Cited

U.S. PATENT DOCUMENTS

| 85,575 A | 1/1869 | Drake |
| 377,588 A | 2/1888 | Walsh, Jr. |

(Continued)

FOREIGN PATENT DOCUMENTS

| AU | 199534570 | 10/1994 |
| AU | 2003239832 | 5/2002 |

(Continued)

OTHER PUBLICATIONS

Christian Pahl, Eberhard Hartung, Anne Grothmann, Katrin Mahlkow-Nerge, Angelika Haeussermann, Rumination activity of dairy cows in the 24 hours before and after calving, Journal of Dairy Science, vol. 97, Issue 11, 2014, pp. 6935-6941.

(Continued)

*Primary Examiner* — Jennifer Robertson
*Assistant Examiner* — Jonathan Drew Moroneso
(74) *Attorney, Agent, or Firm* — Keith O'Doherty

(57) ABSTRACT

The present invention relates to a clamp (3) for handling a device for identifying an animal and/or sampling animal tissue, said clamp (3) comprising two jaws (32, 33), a handle (31) for moving said jaws (32, 33) together, and means (321) for securing an element of said identification and/or sampling device to one of said jaws (32, 33), said securing means (321) being movable between:
  a release position, and
  a securing position.
According to the invention, said clamp (3) comprises actuation means (73) for moving said securing means (321) from (Continued)

one to the other position thereof, said actuation means (73) being actuatable via said handle (31).

18 Claims, 6 Drawing Sheets

(52) U.S. Cl.
CPC ............. *A01K 11/001* (2013.01); *A61B 10/02* (2013.01); *A61B 2503/40* (2013.01)

(56) References Cited

U.S. PATENT DOCUMENTS

| | | |
|---|---|---|
| 584,121 A | 6/1897 | Sanders |
| 818,783 A | 4/1906 | Philippi |
| 823,079 A | 6/1906 | Rais |
| 1,016,752 A | 2/1912 | Leith |
| 1,188,510 A | 6/1916 | Timson |
| 1,364,137 A | 1/1921 | Pannier |
| 1,759,400 A | 5/1930 | Hobbs |
| 1,843,314 A | 2/1932 | Berntson et al. |
| 1,863,037 A | 6/1932 | Archbold |
| 2,078,827 A | 4/1937 | Ketchum |
| 2,420,020 A | 5/1947 | Snell |
| 2,553,400 A | 5/1951 | Blair |
| 2,570,048 A | 10/1951 | Cooke et al. |
| 3,091,770 A | 6/1963 | McMurray et al. |
| 3,261,243 A | 7/1966 | Ellison |
| 3,596,541 A | 8/1971 | Bieganski |
| 3,812,859 A | 5/1974 | Murphy et al. |
| 3,884,100 A | 5/1975 | Fideldy |
| 3,981,209 A | 9/1976 | Caroff |
| 4,030,506 A | 6/1977 | McDonald |
| 4,120,303 A | 10/1978 | Villa-Massone et al. |
| 4,121,591 A | 10/1978 | Hayes |
| 4,281,657 A | 8/1981 | Ritchey |
| 4,323,183 A | 4/1982 | Duchin |
| 4,497,321 A | 2/1985 | Fearing et al. |
| 4,516,577 A | 5/1985 | Scott et al. |
| 4,531,520 A | 7/1985 | Reggers et al. |
| 4,552,147 A | 11/1985 | Gardner |
| 4,666,436 A | 5/1987 | McDonald et al. |
| 4,672,966 A | 6/1987 | Haas, Jr. |
| 4,696,119 A | 9/1987 | Giulie |
| 4,716,899 A | 1/1988 | Huenefeld et al. |
| 4,819,639 A | 4/1989 | Gardner |
| 4,821,683 A | 4/1989 | Veldman |
| 4,943,294 A | 7/1990 | Knapp |
| 5,022,253 A | 6/1991 | Parlatore |
| 5,056,385 A | 10/1991 | Petersen |
| 5,141,514 A | 8/1992 | van Amelsfort |
| 5,154,721 A | 10/1992 | Perez |
| 5,267,464 A | 12/1993 | Cleland |
| 5,509,291 A | 4/1996 | Nilsson et al. |
| 5,651,791 A | 7/1997 | Zavlodaver et al. |
| 5,778,820 A | 7/1998 | van der Lely et al. |
| 6,007,548 A | 12/1999 | Ritchey |
| 6,016,769 A | 1/2000 | Forster |
| 6,043,748 A | 3/2000 | Touchton et al. |
| 6,053,926 A | 4/2000 | Luehrs |
| 6,095,915 A | 8/2000 | Battista et al. |
| 6,099,482 A | 8/2000 | Brune et al. |
| 6,100,804 A | 8/2000 | Brady et al. |
| 6,113,539 A | 9/2000 | Ridenour |
| 6,114,957 A | 9/2000 | Westrick et al. |
| 6,145,225 A | 11/2000 | Ritchey |
| 6,166,643 A | 12/2000 | Janning et al. |
| 6,172,640 B1 | 1/2001 | Durst et al. |
| 6,232,880 B1 | 5/2001 | Anderson et al. |
| 6,235,036 B1 | 5/2001 | Gardner et al. |
| 6,271,757 B1 | 8/2001 | Touchton et al. |
| 6,297,739 B1 | 10/2001 | Small |
| 6,310,553 B1 | 10/2001 | Dance |
| 6,402,692 B1 | 6/2002 | Morford |
| 6,497,197 B1 | 12/2002 | Huisma |
| 6,502,060 B1 | 12/2002 | Christian |
| 6,510,630 B1 | 1/2003 | Gardner |
| 6,535,131 B1 | 3/2003 | Bar-Shalom et al. |
| 6,569,092 B1 | 5/2003 | Booker |
| 6,659,039 B1 | 12/2003 | Larsen |
| 6,868,804 B1 | 3/2005 | Huisma et al. |
| 7,016,730 B2 | 3/2006 | Ternes |
| 7,046,152 B1 | 5/2006 | Peinetti et al. |
| 7,137,359 B1 | 11/2006 | Braden |
| 7,296,539 B2 | 11/2007 | Iljas |
| 7,380,518 B2 | 6/2008 | Kates |
| 7,442,170 B2 * | 10/2008 | Chiu ................. A61B 10/0266 600/564 |
| 7,705,736 B1 | 4/2010 | Kedziora |
| 7,843,350 B2 | 11/2010 | Geissler et al. |
| 7,937,861 B1 | 5/2011 | Zacher |
| 8,005,624 B1 | 8/2011 | Starr |
| 8,266,990 B1 | 9/2012 | Janson |
| 8,305,220 B2 | 11/2012 | Gibson |
| 8,478,389 B1 | 7/2013 | Brockway et al. |
| 8,622,929 B1 | 1/2014 | Wilson et al. |
| 8,763,557 B2 | 7/2014 | Lipscomb |
| 8,955,462 B1 | 2/2015 | Golden et al. |
| 9,215,862 B2 | 12/2015 | Bladen et al. |
| 9,392,767 B2 | 7/2016 | Johnson, III et al. |
| 9,392,946 B2 | 7/2016 | Sarantos et al. |
| 9,449,487 B1 | 9/2016 | Spitalny |
| 9,648,849 B1 | 5/2017 | Vivathana |
| 9,654,925 B1 | 5/2017 | Solinsky et al. |
| 9,693,536 B1 | 7/2017 | Dana |
| 9,717,216 B1 | 8/2017 | Schlachta et al. |
| 9,743,643 B1 | 8/2017 | Kaplan et al. |
| 9,848,577 B1 | 12/2017 | Brandao et al. |
| 9,861,080 B1 | 1/2018 | Hathway et al. |
| 10,021,857 B2 | 7/2018 | Bailey et al. |
| 10,039,263 B2 | 8/2018 | Teychene et al. |
| 10,045,511 B1 | 8/2018 | Yarden et al. |
| 10,064,391 B1 | 9/2018 | Riley |
| 10,091,972 B1 | 10/2018 | Jensen et al. |
| 10,231,442 B1 | 3/2019 | Chang et al. |
| 10,242,547 B1 | 3/2019 | Struhsaker et al. |
| 10,264,762 B1 | 4/2019 | Lamb |
| 10,352,759 B1 | 7/2019 | Jensen |
| 10,446,006 B1 | 10/2019 | Johnson, Jr. et al. |
| 10,512,430 B1 | 12/2019 | Hladio |
| 10,588,295 B1 | 3/2020 | Riley |
| 10,628,756 B1 | 4/2020 | Kuper et al. |
| 10,638,726 B1 | 5/2020 | Makarychev et al. |
| 10,691,674 B2 | 6/2020 | Leong et al. |
| 2001/0027751 A1 | 10/2001 | van den Berg |
| 2002/0010390 A1 | 1/2002 | Guice et al. |
| 2002/0021219 A1 | 2/2002 | Edwards |
| 2002/0091326 A1 | 7/2002 | Hashimoto et al. |
| 2002/0095828 A1 | 7/2002 | Koopman et al. |
| 2002/0154015 A1 | 10/2002 | Hixson |
| 2002/0158765 A1 | 10/2002 | Pape et al. |
| 2003/0004652 A1 | 1/2003 | Brunner et al. |
| 2003/0023517 A1 | 1/2003 | Marsh et al. |
| 2003/0062001 A1 | 4/2003 | Hakan |
| 2003/0066491 A1 | 4/2003 | Stampe |
| 2003/0144926 A1 | 7/2003 | Bodin et al. |
| 2003/0146284 A1 | 8/2003 | Schmit et al. |
| 2003/0149526 A1 | 8/2003 | Zhou et al. |
| 2003/0177025 A1 | 9/2003 | Curkendall et al. |
| 2003/0201931 A1 | 10/2003 | Durst et al. |
| 2003/0208157 A1 | 11/2003 | Eidson et al. |
| 2003/0221343 A1 | 12/2003 | Volk et al. |
| 2003/0229452 A1 | 12/2003 | Lewis |
| 2004/0066298 A1 | 4/2004 | Schmitt et al. |
| 2004/0078390 A1 | 4/2004 | Saunders |
| 2004/0118920 A1 | 6/2004 | He |
| 2004/0123810 A1 | 7/2004 | Lorton et al. |
| 2004/0177011 A1 | 9/2004 | Ramsay et al. |
| 2004/0201454 A1 | 10/2004 | Waterhouse et al. |
| 2005/0010333 A1 | 1/2005 | Lorton et al. |
| 2005/0026181 A1 | 2/2005 | Davis et al. |
| 2005/0097997 A1 | 5/2005 | Hile |
| 2005/0108912 A1 | 5/2005 | Bekker |
| 2005/0115508 A1 | 6/2005 | Little |

(56) References Cited

U.S. PATENT DOCUMENTS

| | | |
|---|---|---|
| 2005/0128086 A1 | 6/2005 | Brown et al. |
| 2005/0139168 A1 | 6/2005 | Light et al. |
| 2005/0145187 A1 | 7/2005 | Gray |
| 2005/0273117 A1 | 12/2005 | Teychene |
| 2005/0279287 A1 | 12/2005 | Kroeker |
| 2005/0284381 A1 | 12/2005 | Bell et al. |
| 2006/0011145 A1 | 1/2006 | Kates |
| 2006/0052986 A1 | 3/2006 | Rogers et al. |
| 2006/0064325 A1 | 3/2006 | Matsumoto et al. |
| 2006/0087440 A1 | 4/2006 | Klein |
| 2006/0106289 A1 | 5/2006 | Elser |
| 2006/0117619 A1 | 6/2006 | Costantini |
| 2006/0155172 A1 | 7/2006 | Rugg |
| 2006/0170561 A1 | 8/2006 | Eyal |
| 2006/0173367 A1 | 8/2006 | Stuart et al. |
| 2006/0185605 A1 | 8/2006 | Renz et al. |
| 2006/0201436 A1 | 9/2006 | Kates |
| 2006/0207515 A1 | 9/2006 | Palett |
| 2006/0241521 A1 | 10/2006 | Cohen |
| 2006/0282274 A1 | 12/2006 | Bennett |
| 2006/0290514 A1 | 12/2006 | Sakama et al. |
| 2007/0006494 A1 | 1/2007 | Hayes et al. |
| 2007/0008155 A1 | 1/2007 | Trost et al. |
| 2007/0021660 A1 | 1/2007 | DeLonzor et al. |
| 2007/0027375 A1 | 2/2007 | Melker et al. |
| 2007/0027377 A1 | 2/2007 | DeLonzor et al. |
| 2007/0027379 A1 | 2/2007 | DeLonzor et al. |
| 2007/0029381 A1 | 2/2007 | Braiman |
| 2007/0044317 A1 | 3/2007 | Critelli |
| 2007/0044732 A1 | 3/2007 | Araki et al. |
| 2007/0062457 A1 | 3/2007 | Bates et al. |
| 2007/0069899 A1 | 3/2007 | Shih et al. |
| 2007/0103296 A1 | 5/2007 | Paessel et al. |
| 2007/0149871 A1 | 6/2007 | Sarussi et al. |
| 2007/0152825 A1 | 7/2007 | August et al. |
| 2007/0222624 A1 | 9/2007 | Eicken et al. |
| 2007/0255124 A1 | 11/2007 | Pologe et al. |
| 2007/0258625 A1 | 11/2007 | Mirtsching |
| 2007/0283791 A1 | 12/2007 | Engvall et al. |
| 2007/0298421 A1 | 12/2007 | Jiang et al. |
| 2008/0001815 A1 | 1/2008 | Wang et al. |
| 2008/0004798 A1 | 1/2008 | Troxler et al. |
| 2008/0017126 A1 | 1/2008 | Adams et al. |
| 2008/0018481 A1 | 1/2008 | Zehavi |
| 2008/0021352 A1 | 1/2008 | Keegan et al. |
| 2008/0036610 A1 | 2/2008 | Hokuf et al. |
| 2008/0047177 A1 | 2/2008 | Hilpert |
| 2008/0055155 A1 | 3/2008 | Hensley et al. |
| 2008/0059263 A1 | 3/2008 | Stroman et al. |
| 2008/0061990 A1 | 3/2008 | Milnes et al. |
| 2008/0076988 A1 | 3/2008 | Sarussi et al. |
| 2008/0076992 A1 | 3/2008 | Hete et al. |
| 2008/0085522 A1 | 4/2008 | Meghen et al. |
| 2008/0097726 A1 | 4/2008 | Lorton et al. |
| 2008/0110406 A1 | 5/2008 | Anderson et al. |
| 2008/0146890 A1 | 6/2008 | LeBoeuf et al. |
| 2008/0173255 A1 | 7/2008 | Mainini et al. |
| 2008/0190202 A1 | 8/2008 | Kulach et al. |
| 2008/0190379 A1 | 8/2008 | Mainini et al. |
| 2008/0215484 A1 | 9/2008 | Oldham |
| 2008/0227662 A1 | 9/2008 | Stromberg et al. |
| 2008/0228105 A1 | 9/2008 | Howell et al. |
| 2008/0262326 A1 | 10/2008 | Hete et al. |
| 2008/0272908 A1 | 11/2008 | Boyd |
| 2008/0312511 A1 | 12/2008 | Osler et al. |
| 2009/0009388 A1 | 1/2009 | Wangrud |
| 2009/0020613 A1 | 1/2009 | Chang et al. |
| 2009/0025651 A1 | 1/2009 | Lalor |
| 2009/0058730 A1 | 3/2009 | Geissler et al. |
| 2009/0094869 A1 | 4/2009 | Geissler et al. |
| 2009/0102668 A1 | 4/2009 | Thompson et al. |
| 2009/0139462 A1 | 6/2009 | So |
| 2009/0149727 A1 | 6/2009 | Truitt et al. |
| 2009/0187392 A1 | 7/2009 | Riskey et al. |
| 2009/0255484 A1 | 10/2009 | Muelken |
| 2009/0312667 A1 | 12/2009 | Utsunomiya et al. |
| 2010/0018363 A1 | 1/2010 | Chervenak et al. |
| 2010/0030036 A1 | 2/2010 | Mottram et al. |
| 2010/0045468 A1 | 2/2010 | Geissler |
| 2010/0113902 A1 | 5/2010 | Hete et al. |
| 2010/0139575 A1 | 6/2010 | Duncan et al. |
| 2010/0160809 A1 | 6/2010 | Laurence et al. |
| 2010/0175625 A1 | 7/2010 | Klenotiz |
| 2010/0217102 A1 | 8/2010 | LeBoeuf et al. |
| 2010/0250198 A1 | 9/2010 | Lorton et al. |
| 2010/0289639 A1 | 11/2010 | Gibson et al. |
| 2010/0315241 A1 | 12/2010 | Jow |
| 2010/0321182 A1 | 12/2010 | Wangrud |
| 2010/0321189 A1 | 12/2010 | Gibson et al. |
| 2010/0331739 A1 | 12/2010 | Maltz et al. |
| 2011/0018717 A1 | 1/2011 | Takahashi et al. |
| 2011/0061605 A1 | 3/2011 | Hardi et al. |
| 2011/0095089 A1 | 4/2011 | Kolton et al. |
| 2011/0121356 A1 | 5/2011 | Krawinkel et al. |
| 2011/0137185 A1 | 6/2011 | Hete et al. |
| 2011/0152876 A1 | 6/2011 | Vandeputte |
| 2011/0178423 A1 | 7/2011 | Hatch |
| 2011/0203144 A1 | 8/2011 | Junek et al. |
| 2011/0258130 A1 | 10/2011 | Grabiner et al. |
| 2011/0272470 A1 | 11/2011 | Baba et al. |
| 2011/0313264 A1 | 12/2011 | Hete et al. |
| 2012/0009943 A1 | 1/2012 | Greenberg et al. |
| 2012/0068848 A1 | 3/2012 | Campbell et al. |
| 2012/0089152 A1 | 4/2012 | Lynd et al. |
| 2012/0092132 A1 | 4/2012 | Holme et al. |
| 2012/0111286 A1 | 5/2012 | Lee et al. |
| 2012/0112917 A1 | 5/2012 | Menachem et al. |
| 2012/0160181 A1 | 6/2012 | So et al. |
| 2012/0175412 A1 | 7/2012 | Grabiner et al. |
| 2012/0204811 A1 | 8/2012 | Ryan |
| 2012/0236690 A1 | 9/2012 | Rader et al. |
| 2012/0291715 A1 | 11/2012 | Jiang et al. |
| 2012/0299731 A1 | 11/2012 | Triener |
| 2012/0326862 A1 | 12/2012 | Kwak et al. |
| 2012/0326874 A1 | 12/2012 | Kwak et al. |
| 2013/0006065 A1 | 1/2013 | Yanai et al. |
| 2013/0014706 A1 | 1/2013 | Menkes |
| 2013/0046170 A1 | 2/2013 | Haynes |
| 2013/0113622 A1 | 5/2013 | Pratt et al. |
| 2013/0119142 A1 | 5/2013 | McCoy et al. |
| 2013/0175347 A1 | 7/2013 | Decaluwe et al. |
| 2013/0192526 A1 | 8/2013 | Mainini |
| 2013/0204159 A1* | 8/2013 | Destoumieux ...... A61B 10/0266 600/564 |
| 2013/0211773 A1 | 8/2013 | Loeschinger et al. |
| 2013/0222141 A1 | 8/2013 | Rhee et al. |
| 2013/0237778 A1 | 9/2013 | Rouquette et al. |
| 2013/0239904 A1 | 9/2013 | Kim et al. |
| 2013/0239907 A1 | 9/2013 | Laurence et al. |
| 2013/0265165 A1 | 10/2013 | So et al. |
| 2013/0285815 A1 | 10/2013 | Jones, II |
| 2014/0073486 A1 | 3/2014 | Ahmed et al. |
| 2014/0122488 A1 | 5/2014 | Jung et al. |
| 2014/0123912 A1 | 5/2014 | Menkes et al. |
| 2014/0135596 A1 | 5/2014 | LeBoeuf et al. |
| 2014/0135631 A1 | 5/2014 | Brumback et al. |
| 2014/0171762 A1 | 6/2014 | LeBoeuf et al. |
| 2014/0174376 A1 | 6/2014 | Touchton et al. |
| 2014/0196673 A1 | 7/2014 | Menkes et al. |
| 2014/0230755 A1 | 8/2014 | Trenkle et al. |
| 2014/0232541 A1 | 8/2014 | Trenkle et al. |
| 2014/0253709 A1 | 9/2014 | Bresch et al. |
| 2014/0261235 A1 | 9/2014 | Rich et al. |
| 2014/0267299 A1 | 9/2014 | Couse |
| 2014/0275824 A1 | 9/2014 | Couse |
| 2014/0276089 A1 | 9/2014 | Kirenko et al. |
| 2014/0290013 A1 | 10/2014 | Eidelman et al. |
| 2014/0302783 A1 | 10/2014 | Aiuto et al. |
| 2014/0331942 A1 | 11/2014 | Sarazyn |
| 2014/0333439 A1 | 11/2014 | Downing et al. |
| 2014/0347184 A1 | 11/2014 | Triener |
| 2014/0352632 A1 | 12/2014 | McLaughlin |
| 2014/0368338 A1 | 12/2014 | Rettedal et al. |
| 2015/0025394 A1 | 1/2015 | Hong et al. |

(56) References Cited

U.S. PATENT DOCUMENTS

| | | |
|---|---|---|
| 2015/0039239 A1 | 2/2015 | Shuler et al. |
| 2015/0057963 A1 | 2/2015 | Zakharov et al. |
| 2015/0097668 A1 | 4/2015 | Toth |
| 2015/0099472 A1 | 4/2015 | Ickovic |
| 2015/0100245 A1 | 4/2015 | Huang et al. |
| 2015/0107519 A1 | 4/2015 | Rajkondawar et al. |
| 2015/0107522 A1 | 4/2015 | Lamb |
| 2015/0122893 A1 | 5/2015 | Warther |
| 2015/0128873 A1 | 5/2015 | Prescott et al. |
| 2015/0130617 A1 | 5/2015 | Triener |
| 2015/0148811 A1 | 5/2015 | Swope et al. |
| 2015/0157435 A1 | 6/2015 | Chasins et al. |
| 2015/0182322 A1 | 7/2015 | Couse et al. |
| 2015/0245592 A1 | 9/2015 | Sibbald et al. |
| 2015/0282457 A1 | 10/2015 | Yarden |
| 2015/0334994 A1 | 11/2015 | Prasad |
| 2015/0342143 A1 | 12/2015 | Stewart |
| 2015/0351885 A1 | 12/2015 | Kool et al. |
| 2015/0366166 A1 | 12/2015 | Mueller |
| 2016/0000045 A1 | 1/2016 | Funaya et al. |
| 2016/0021506 A1 | 1/2016 | Bonge, Jr. |
| 2016/0058379 A1 | 3/2016 | Menkes et al. |
| 2016/0066546 A1 | 3/2016 | Borchersen et al. |
| 2016/0100802 A1 | 4/2016 | Newman |
| 2016/0106064 A1 | 4/2016 | Bladen et al. |
| 2016/0113524 A1 | 4/2016 | Gross et al. |
| 2016/0120154 A1 | 5/2016 | Hill et al. |
| 2016/0128637 A1 | 5/2016 | LeBoeuf et al. |
| 2016/0135431 A1 | 5/2016 | Sheldon et al. |
| 2016/0148086 A1 | 5/2016 | Clarke et al. |
| 2016/0150362 A1 | 5/2016 | Shaprio et al. |
| 2016/0151013 A1 | 6/2016 | Atallah et al. |
| 2016/0165851 A1 | 6/2016 | Harty et al. |
| 2016/0165852 A1 | 6/2016 | Goldfain |
| 2016/0166761 A1 | 6/2016 | Piehl et al. |
| 2016/0198957 A1 | 7/2016 | Arditi et al. |
| 2016/0210841 A1 | 7/2016 | Huang et al. |
| 2016/0213317 A1 | 7/2016 | Richardson et al. |
| 2016/0278712 A1 | 9/2016 | Sagara et al. |
| 2016/0286757 A1 | 10/2016 | Armstrong |
| 2016/0287108 A1 | 10/2016 | Wei et al. |
| 2016/0317049 A1 | 11/2016 | LeBoeuf et al. |
| 2016/0345881 A1 | 12/2016 | Sarantos et al. |
| 2016/0360733 A1 | 12/2016 | Triener |
| 2016/0367495 A1 | 12/2016 | Miller et al. |
| 2017/0000090 A1 | 1/2017 | Hall |
| 2017/0006836 A1 | 1/2017 | Torres |
| 2017/0042119 A1 | 2/2017 | Garrity |
| 2017/0067770 A1 | 3/2017 | Sun |
| 2017/0079247 A1 | 3/2017 | Womble et al. |
| 2017/0095206 A1 | 4/2017 | Leib et al. |
| 2017/0156288 A1 | 6/2017 | Singh |
| 2017/0164905 A1 | 6/2017 | Pinney Wood et al. |
| 2017/0193208 A1 | 7/2017 | Ashley et al. |
| 2017/0196203 A1 | 7/2017 | Huisma et al. |
| 2017/0202185 A1 | 7/2017 | Trumbull et al. |
| 2017/0245797 A1 | 8/2017 | Quinn |
| 2017/0258039 A1 | 9/2017 | Lauterbach |
| 2017/0272842 A1 | 9/2017 | Touma |
| 2017/0280675 A1 | 10/2017 | MacNeil et al. |
| 2017/0280688 A1 | 10/2017 | Deliou et al. |
| 2017/0318781 A1 | 11/2017 | Noertker et al. |
| 2017/0360004 A1 | 12/2017 | Carver |
| 2017/0372583 A1 | 12/2017 | Lamkin et al. |
| 2018/0000045 A1 | 1/2018 | Bianchi et al. |
| 2018/0007863 A1 | 1/2018 | Bailey et al. |
| 2018/0014512 A1 | 1/2018 | Arabani et al. |
| 2018/0055016 A1 | 3/2018 | Hsieh et al. |
| 2018/0064068 A1 | 3/2018 | McKee et al. |
| 2018/0070559 A1 | 3/2018 | So |
| 2018/0098522 A1 | 4/2018 | Steinfort |
| 2018/0110205 A1 | 4/2018 | Czarnecky et al. |
| 2018/0131074 A1 | 5/2018 | Wilkinson et al. |
| 2018/0132455 A1 | 5/2018 | Pradeep et al. |
| 2018/0206455 A1 | 7/2018 | Thiex et al. |
| 2018/0242860 A1 | 8/2018 | LeBoeuf et al. |
| 2018/0249683 A1 | 9/2018 | Borchersen et al. |
| 2018/0260976 A1 | 9/2018 | Watanabe et al. |
| 2018/0271058 A1 | 9/2018 | Valdez |
| 2018/0279582 A1 | 10/2018 | Yajima et al. |
| 2018/0288968 A1 | 10/2018 | Cisco |
| 2018/0295809 A1 | 10/2018 | Yajima et al. |
| 2018/0303425 A1 | 10/2018 | Wordham et al. |
| 2018/0310526 A1 | 11/2018 | Birch et al. |
| 2018/0325382 A1 | 11/2018 | Brandao et al. |
| 2018/0332989 A1 | 11/2018 | Chiu et al. |
| 2018/0333244 A1 | 11/2018 | Hanks et al. |
| 2019/0008118 A1 | 1/2019 | Keegan |
| 2019/0008124 A1 | 1/2019 | Komatsu et al. |
| 2019/0029226 A1 | 1/2019 | Triener |
| 2019/0053469 A1 | 2/2019 | Mardirossian |
| 2019/0053470 A1 | 2/2019 | Singh et al. |
| 2019/0059335 A1 | 2/2019 | Crider, Jr. et al. |
| 2019/0059337 A1 | 2/2019 | Robbins |
| 2019/0059741 A1 | 2/2019 | Crider, Jr. et al. |
| 2019/0069512 A1 | 3/2019 | Eriksson et al. |
| 2019/0075945 A1 | 3/2019 | Strassburger et al. |
| 2019/0082654 A1 | 3/2019 | Robbins |
| 2019/0090754 A1 | 3/2019 | Brandao et al. |
| 2019/0110433 A1 | 4/2019 | Myers |
| 2019/0110436 A1 | 4/2019 | Gardner et al. |
| 2019/0125509 A1 | 5/2019 | Hotchkin |
| 2019/0130728 A1 | 5/2019 | Struhsaker et al. |
| 2019/0133086 A1 | 5/2019 | Katz et al. |
| 2019/0159428 A1 | 5/2019 | Bolen |
| 2019/0166802 A1 | 6/2019 | Seltzer et al. |
| 2019/0183091 A1 | 6/2019 | Betts-LaCroix et al. |
| 2019/0183092 A1 | 6/2019 | Couse et al. |
| 2019/0208358 A1 | 7/2019 | de Barros Chapiewski et al. |
| 2019/0213860 A1 | 7/2019 | Shaprio et al. |
| 2019/0254599 A1 | 8/2019 | Young et al. |
| 2019/0287429 A1 | 9/2019 | Dawson et al. |
| 2019/0290133 A1 | 9/2019 | Crider et al. |
| 2019/0290847 A1 | 9/2019 | Veyrent et al. |
| 2019/0298226 A1 | 10/2019 | Filipowicz |
| 2019/0298924 A1 | 10/2019 | Gibson et al. |
| 2019/0327939 A1 | 10/2019 | Sharpe et al. |
| 2019/0335715 A1 | 11/2019 | Hicks et al. |
| 2019/0350168 A1 | 11/2019 | Shi |
| 2019/0365324 A1 | 12/2019 | Chang |
| 2019/0373857 A1 | 12/2019 | Leigh-Lancaster et al. |
| 2019/0380311 A1 | 12/2019 | Crouthamel et al. |
| 2019/0385037 A1 | 12/2019 | Robadey et al. |
| 2019/0385332 A1 | 12/2019 | Yajima et al. |
| 2020/0015740 A1 | 1/2020 | Alnofeli et al. |
| 2020/0037886 A1 | 2/2020 | Greer et al. |
| 2020/0068853 A1 | 3/2020 | Radovcic |
| 2020/0085019 A1 | 3/2020 | Gilbert et al. |
| 2020/0100463 A1 | 4/2020 | Rooda et al. |
| 2020/0107522 A1 | 4/2020 | Kersey et al. |
| 2020/0110946 A1 | 4/2020 | Kline et al. |
| 2020/0113728 A1 | 4/2020 | Spector et al. |
| 2020/0170222 A1 | 6/2020 | Gotts |
| 2020/0178505 A1 | 6/2020 | Womble et al. |
| 2020/0178800 A1 | 6/2020 | Geissler et al. |
| 2020/0205381 A1 | 7/2020 | Wernimont et al. |
| 2020/0229391 A1 | 7/2020 | De Groot |
| 2020/0229707 A1 | 7/2020 | Donnelly |
| 2020/0242551 A1 | 7/2020 | Lau et al. |

FOREIGN PATENT DOCUMENTS

| | | |
|---|---|---|
| AU | 2003238759 | 1/2004 |
| AU | 2004263067 | 2/2005 |
| AU | 2004305403 | 7/2005 |
| AU | 2011210083 | 8/2011 |
| AU | 2016266101 | 12/2016 |
| AU | 2017100469 | 5/2017 |
| AU | 2018220079 | 9/2018 |
| BR | MU8701673 | 3/2009 |
| BR | 112012018909 | 1/2011 |
| CA | 2267812 | 10/2000 |
| CA | 2493331 | 1/2005 |
| CA | 2788153 | 8/2011 |

(56) References Cited

FOREIGN PATENT DOCUMENTS

| | | |
|---|---|---|
| CA | 2880138 | 2/2013 |
| CA | 2858905 | 10/2013 |
| CA | 2875637 | 1/2014 |
| CA | 2875578 | 12/2014 |
| CA | 2915843 | 12/2014 |
| CA | 2990620 | 12/2016 |
| CA | 2916286 | 6/2017 |
| CA | 3007296 | 6/2017 |
| CN | 1989895 | 7/2007 |
| CN | 201171316 | 12/2008 |
| CN | 101578516 | 11/2009 |
| CN | 101816290 | 9/2010 |
| CN | 101875975 | 11/2010 |
| CN | 101875976 | 11/2010 |
| CN | 102781225 | 1/2011 |
| CN | 102142116 | 8/2011 |
| CN | 102485892 | 6/2012 |
| CN | 102682322 | 9/2012 |
| CN | 203313865 | 12/2013 |
| CN | 203689049 | 2/2014 |
| CN | 203523519 | 4/2014 |
| CN | 204047531 | 8/2014 |
| CN | 204305813 | 5/2015 |
| CN | 204331349 | 5/2015 |
| CN | 105191817 | 12/2015 |
| CN | 106125648 | 11/2016 |
| CN | 106172068 | 12/2016 |
| CN | 106197675 | 12/2016 |
| CN | 106719037 | 2/2017 |
| CN | 205919898 | 2/2017 |
| CN | 106472347 | 3/2017 |
| CN | 106845598 | 6/2017 |
| CN | 206431665 | 8/2017 |
| CN | 107201409 | 9/2017 |
| CN | 207201674 | 9/2017 |
| CN | 107251851 | 10/2017 |
| CN | 107667898 | 2/2018 |
| CN | 108353810 | 2/2018 |
| CN | 207100094 | 3/2018 |
| CN | 207249710 | 4/2018 |
| CN | 108651301 | 5/2018 |
| CN | 108656996 | 5/2018 |
| CN | 108684549 | 5/2018 |
| CN | 108118096 | 6/2018 |
| CN | 108308055 | 7/2018 |
| CN | 109006541 | 8/2018 |
| CN | 109008529 | 8/2018 |
| CN | 108617533 | 10/2018 |
| CN | 108717668 | 10/2018 |
| CN | 108766586 | 11/2018 |
| CN | 109006550 | 12/2018 |
| CN | 208273869 | 12/2018 |
| CN | 109355402 | 2/2019 |
| CN | 109937904 | 3/2019 |
| CN | 109937905 | 3/2019 |
| CN | 109823691 | 5/2019 |
| CN | 110073995 | 5/2019 |
| CN | 110059781 | 7/2019 |
| CN | 110106261 | 8/2019 |
| CN | 110106262 | 8/2019 |
| CN | 110506656 | 11/2019 |
| CN | 210076292 | 2/2020 |
| DE | 633742 | 8/1936 |
| DE | 2850438 | 5/1980 |
| DE | 19629166 | 2/1997 |
| DE | 19826348 | 6/1998 |
| DE | 29906146 | 6/1999 |
| DE | 19911766 | 9/2000 |
| DE | 20018364 | 1/2001 |
| DE | 10001176 | 5/2001 |
| DE | 102004027978 | 12/2005 |
| DE | 20201000832 | 2/2012 |
| DE | 202013011075 | 1/2014 |
| DE | 202016101289 | 4/2016 |
| DK | 140001 | 11/1979 |
| EP | 55127 | 6/1982 |
| EP | 125915 | 11/1984 |
| EP | 0499428 | 8/1992 |
| EP | 513525 | 11/1992 |
| EP | 743043 | 11/1996 |
| EP | 938841 | 2/1998 |
| EP | 898449 | 3/1999 |
| EP | 1076485 | 2/2001 |
| EP | 1445723 | 8/2004 |
| EP | 1479338 | 11/2004 |
| EP | 1521208 | 4/2005 |
| EP | 1907816 | 4/2008 |
| EP | 1961294 | 8/2008 |
| EP | 2028931 | 3/2009 |
| EP | 2172878 | 4/2010 |
| EP | 2453733 | 5/2012 |
| EP | 2465344 | 6/2012 |
| EP | 2488237 | 8/2012 |
| EP | 2528431 | 12/2012 |
| EP | 2534945 | 12/2012 |
| EP | 2657889 | 10/2013 |
| EP | 2664234 | 11/2013 |
| EP | 2728995 | 5/2014 |
| EP | 2879615 | 6/2015 |
| EP | 2955998 | 12/2015 |
| EP | 3153098 | 4/2017 |
| EP | 3164855 | 5/2017 |
| EP | 3210531 | 8/2017 |
| EP | 3217566 | 9/2017 |
| EP | 3218865 | 9/2017 |
| EP | 3225106 | 10/2017 |
| EP | 3316680 | 5/2018 |
| EP | 3346422 | 7/2018 |
| EP | 3385886 | 10/2018 |
| EP | 3593634 | 1/2020 |
| EP | 3627856 | 3/2020 |
| EP | 3660855 | 6/2020 |
| ES | 2046912 | 2/1994 |
| ES | 2206009 | 5/2004 |
| ES | 2215152 | 10/2004 |
| ES | 1072416 | 7/2010 |
| ES | 2391341 | 11/2012 |
| ES | 1194609 | 10/2017 |
| FI | 20165318 | 6/2017 |
| FR | 2106705 | 5/1972 |
| FR | 2297565 | 8/1976 |
| FR | 2342024 | 1/1983 |
| FR | 2601848 | 1/1988 |
| FR | 2779153 | 12/1999 |
| FR | 2834521 | 7/2003 |
| FR | 2964777 | 3/2012 |
| FR | 3046332 | 1/2016 |
| FR | 3024653 | 2/2016 |
| FR | 3085249 | 9/2018 |
| GB | 588870 | 6/1947 |
| GB | 641394 | 8/1950 |
| GB | 865164 | 4/1961 |
| GB | 1072971 | 6/1967 |
| GB | 1267830 | 3/1972 |
| GB | 1415650 | 11/1975 |
| GB | 2044684 A | 10/1980 |
| GB | 2067121 | 7/1981 |
| GB | 2055670 | 7/1983 |
| GB | 2114045 | 8/1983 |
| GB | 2125343 | 3/1984 |
| GB | 2142812 | 1/1985 |
| GB | 2392138 | 2/2004 |
| GB | 2469326 | 10/2010 |
| GB | 2554636 | 9/2016 |
| GB | 2570340 | 7/2019 |
| GB | 2571404 | 8/2019 |
| IN | 201103443 | 12/2011 |
| IN | 200802272 | 6/2016 |
| JP | 57173562 | 11/1982 |
| JP | 7177832 | 7/1995 |
| JP | 2001178692 | 7/2001 |
| JP | 2004292151 | 10/2004 |
| JP | 2005102959 | 4/2005 |
| JP | 5659243 | 1/2011 |

(56) References Cited

FOREIGN PATENT DOCUMENTS

| | | |
|---|---|---|
| JP | 2011067178 | 4/2011 |
| JP | 2011087657 | 5/2011 |
| JP | 2013247941 | 6/2012 |
| JP | 2017112857 | 6/2017 |
| JP | 2017002170 | 4/2018 |
| KR | 2003061157 | 7/2003 |
| KR | 2005046330 | 5/2005 |
| KR | 780449 | 11/2007 |
| KR | 101747418 | 1/2011 |
| KR | 20130019970 | 2/2013 |
| KR | 20130057683 | 6/2013 |
| KR | 2013138899 | 12/2013 |
| KR | 2019061805 | 11/2017 |
| KR | 101827311 | 2/2018 |
| KR | 20180035537 | 4/2018 |
| KR | 2018109451 | 10/2018 |
| KR | 20190081598 | 7/2019 |
| KR | 2019091708 | 8/2019 |
| MX | 9600754 | 2/1997 |
| MX | 356331 | 1/2011 |
| NL | 2017104 | 1/2018 |
| NL | 2019186 | 1/2019 |
| NL | 2020275 | 7/2019 |
| NZ | 198486 | 5/1986 |
| NZ | 199494 | 7/1986 |
| NZ | 203924 | 10/1986 |
| NZ | 335702 | 3/2001 |
| NZ | 507129 | 8/2002 |
| NZ | 582984 | 1/2011 |
| RU | 2178711 | 1/2002 |
| RU | 2265324 | 12/2005 |
| SE | 4567 | 3/1893 |
| SE | 5549 | 4/1894 |
| SE | 123213 | 11/1948 |
| SE | 188102 | 3/1964 |
| SU | 1766336 | 10/1992 |
| WO | 1984000468 | 2/1984 |
| WO | 1991011956 | 8/1991 |
| WO | 199302549 | 2/1993 |
| WO | 199822028 | 5/1998 |
| WO | 1998039475 | 9/1998 |
| WO | 1999017658 | 4/1999 |
| WO | 2000062263 | 4/1999 |
| WO | 9945761 | 9/1999 |
| WO | 2000013393 | 3/2000 |
| WO | 2000061802 | 10/2000 |
| WO | 2001033950 | 5/2001 |
| WO | WO0172117 A1 | 10/2001 |
| WO | 2001087054 | 11/2001 |
| WO | 2002031629 | 4/2002 |
| WO | 2002085106 | 10/2002 |
| WO | 2003001180 | 1/2003 |
| WO | 2004092920 | 3/2003 |
| WO | 2003087765 | 10/2003 |
| WO | 2003094605 | 11/2003 |
| WO | 2004015655 | 2/2004 |
| WO | 2005104775 | 4/2004 |
| WO | 2006078943 | 1/2005 |
| WO | 2005104930 | 4/2005 |
| WO | 2005073408 | 8/2005 |
| WO | 2006021855 | 3/2006 |
| WO | 2006134197 | 12/2006 |
| WO | 2006135265 | 12/2006 |
| WO | 2007034211 | 3/2007 |
| WO | 2007095684 | 8/2007 |
| WO | 2007122375 | 11/2007 |
| WO | 2008033042 | 3/2008 |
| WO | 2008041839 A1 | 4/2008 |
| WO | 2008052298 | 5/2008 |
| WO | 2008075974 | 6/2008 |
| WO | 2010091686 | 12/2008 |
| WO | 2009034497 | 3/2009 |
| WO | 2009062249 | 5/2009 |
| WO | 2009076325 | 6/2009 |
| WO | 2009089215 | 7/2009 |
| WO | 2009117764 | 10/2009 |
| WO | WO2009127541 A1 | 10/2009 |
| WO | 2009153779 | 12/2009 |
| WO | 2010008620 | 1/2010 |
| WO | 2010048753 | 5/2010 |
| WO | 2010053811 | 5/2010 |
| WO | 2010068713 | 6/2010 |
| WO | 2010140900 | 12/2010 |
| WO | 2012075480 | 12/2010 |
| WO | 2011039112 | 4/2011 |
| WO | 2011076886 | 6/2011 |
| WO | 2011154949 | 12/2011 |
| WO | WO2012013429 A1 | 2/2012 |
| WO | 2012071670 | 6/2012 |
| WO | 2013008115 | 1/2013 |
| WO | 2013038326 | 3/2013 |
| WO | 2013082227 | 6/2013 |
| WO | 2015001537 | 7/2013 |
| WO | 2013118121 | 8/2013 |
| WO | 2015024050 | 8/2013 |
| WO | 2013179020 | 12/2013 |
| WO | 2013190423 | 12/2013 |
| WO | 2014020463 | 2/2014 |
| WO | 2014095759 | 6/2014 |
| WO | 2014107766 | 7/2014 |
| WO | 2014118788 | 8/2014 |
| WO | 2014125250 | 8/2014 |
| WO | 2016027271 | 8/2014 |
| WO | 2014140148 | 9/2014 |
| WO | 2014141084 | 9/2014 |
| WO | 2014194383 | 12/2014 |
| WO | 2014197631 | 12/2014 |
| WO | 2014199363 | 12/2014 |
| WO | 2015009167 | 1/2015 |
| WO | 2015030832 | 3/2015 |
| WO | 2015055709 | 4/2015 |
| WO | 2015086338 | 6/2015 |
| WO | 2016207844 | 6/2015 |
| WO | 2015107354 | 7/2015 |
| WO | 2017001717 | 7/2015 |
| WO | 2017031532 | 8/2015 |
| WO | 2015140486 | 9/2015 |
| WO | 2015158787 | 10/2015 |
| WO | 2015175686 | 11/2015 |
| WO | 2015176027 | 11/2015 |
| WO | 2015197385 | 12/2015 |
| WO | 2016037190 | 3/2016 |
| WO | 2017149049 | 3/2016 |
| WO | 2016053104 | 4/2016 |
| WO | 2016108187 | 7/2016 |
| WO | 2016166748 | 10/2016 |
| WO | 2017001538 | 1/2017 |
| WO | 2017027551 | 2/2017 |
| WO | 2017037479 | 3/2017 |
| WO | 2017066813 | 4/2017 |
| WO | 2017089289 | 6/2017 |
| WO | 2017096256 | 6/2017 |
| WO | 2017121834 | 7/2017 |
| WO | 2018006965 | 1/2018 |
| WO | 2018011736 | 1/2018 |
| WO | 2018019742 | 2/2018 |
| WO | 2020022543 | 7/2018 |
| WO | 2018172976 | 9/2018 |
| WO | 2020060248 | 9/2018 |
| WO | 2018203203 | 11/2018 |
| WO | 2019009717 | 1/2019 |
| WO | 2019025138 | 2/2019 |
| WO | 2019046216 | 3/2019 |
| WO | 2019048521 A1 | 3/2019 |
| WO | 2019058752 | 3/2019 |
| WO | 2019071222 | 4/2019 |
| WO | 2019132803 | 7/2019 |
| WO | 2019207561 | 10/2019 |
| WO | 2019235942 | 12/2019 |
| WO | 2019245978 | 12/2019 |
| WO | 2020003310 | 1/2020 |

(56) References Cited

FOREIGN PATENT DOCUMENTS

| WO | 2020096528 | 5/2020 |
|---|---|---|
| WO | 2020140013 | 7/2020 |

OTHER PUBLICATIONS

Steensels, Machteld; Maltz, Ephraim; Bahr, Claudia; Berckmans, Daniel; Antler, Aharon; et al., Towards practical application of sensors for monitoring animal health: The effect of post-calving health problems on rumination duration, activity and milk yield, The Journal of Dairy Research; Cambridge vol. 84, Iss. 2, (May 2017): 132-138.

Clark, C., Lyons, N., Millapan, L., Talukder, S., Cronin, G., Kerrisk, K., & Garcia, S. (2015), Rumination and activity levels as predictors of calving for dairy cows, Animal, 9(4), 691-695.

K. Koyama, T. Koyama, M. Sugimoto, N. Kusakari, R. Miura, K. Yoshioka, M. Hirako, Prediction of calving time in Holstein dairy cows by monitoring the ventral tail base surface temperature, The Veterinary Journal, vol. 240, 2018, pp. 1-5, ISSN 1090-0233.

L. Calamari, N. Soriani, G. Panella, F. Petrera, A. Minuti, E. Trevisi, Rumination time around calving: An early signal to detect cows at greater risk of disease, Journal of Dairy Science, vol. 97, Issue 6, 2014, pp. 3635-3647, ISSN 0022-0302.

S. Benaissa, F.A.M. Tuyttens, D. Plets, J. Trogh, L. Martens, L. Vandaele, W. Joseph, B. Sonck, Calving and estrus detection in dairy cattle using a combination of indoor localization and accelerometer sensors, Computers and Electronics in Agriculture, vol. 168, 2020, 105153, ISSN 0168-1699.

N. Soriani, E. Trevisi, L. Calamari, Relationships between rumination time, metabolic conditions, and health status in dairy cows during the transition period, Journal of Animal Science, vol. 90, Issue 12, Dec. 2012, pp. 4544-4554.

The role of sensors, big data and machine learning in modern animal farming; Suresh Neethirajan; Received Jun. 2, 2020; Received in revised form Jun. 30, 2020; Accepted Jul. 3, 2020 Sensing and Bio-Sensing Research 29 (2020) 1003672214-1804/ © 2020 The Author. Published by Elsevier B.V.

A Review on Determination of Computer Aid Diagnosis and/or Risk Factors Using Data Mining Methods in Veterinary Field Pinar Cihan, Erhan Gökçe, Oya Kalipsiz; Tekirdağ Namk Kemal University, Çorlu Faculty of Engineering, Department of Computer Engineering, Tekirdağ, Turkey. 2019.

Big Data Analytics and Precision Animal Agriculture Symposium: Data to decisions B. J. White, D. E. Amrine, and R. L. Larson Beef Cattle Institute, Kansas State University, Manhattan, KS; © The Author(s) 2018. Published by Oxford University Press on behalf of American Society of Animal Science.

Gasteiner, J.; Boswerger, B.; Guggenberger, T., Practical use of a novel ruminal sensor on dairy farms, Praktische Tierarzt 2012 vol. 93 No. 8 pp. 730 . . . 739 ref.45.

Drying up Cows and The Effect of Different Methods Upon Milk Production; Ralph Wayne, C. H. Eckles, and W. E. Peterson; Division of Dairy Husbandry, University of Minnesota, St. Paul; Research-Articlelvol. 16, Issue 1, p. 69-78, Jan. 1, 1933.

\* cited by examiner

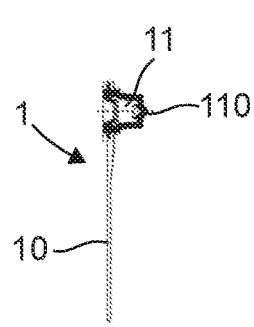
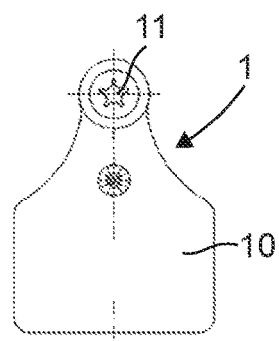
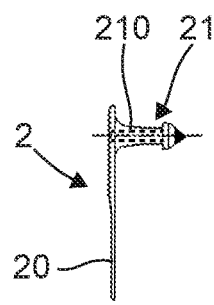
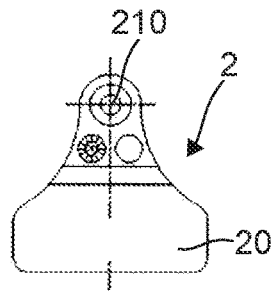
Fig. 1b    Fig. 1a    Fig. 2b    Fig. 2a
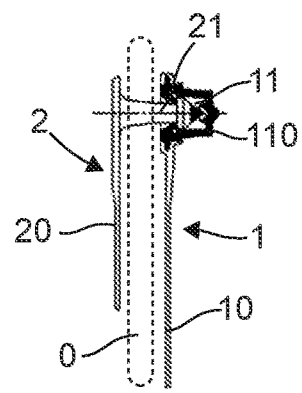
Fig. 4
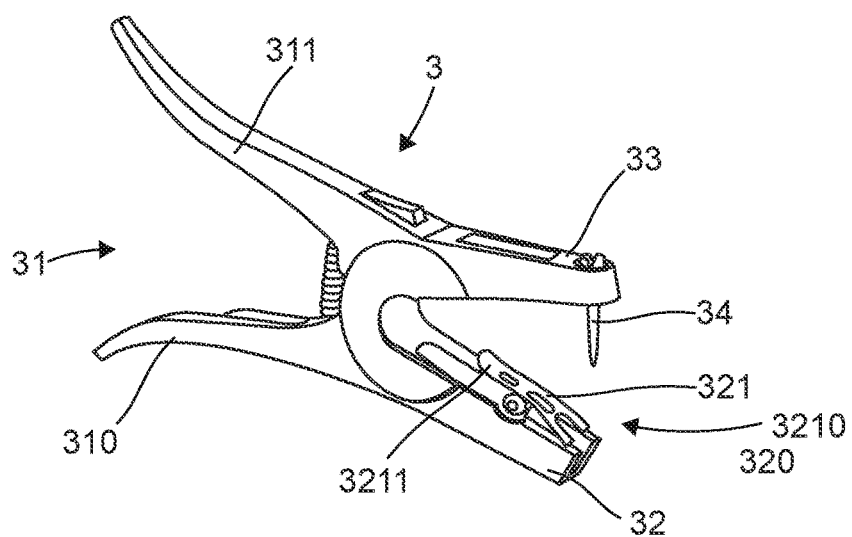
Fig. 3

GRIPPER FOR MANIPULATING A DEVICE FOR IDENTIFYING AN ANIMAL AND/OR REMOVING TISSUE FROM AN ANIMAL COMPRISING HOLDING MEANS WITH REMOTE ACTUATION

1. FIELD OF THE INVENTION

The invention relates to the field of design and manufacture of clamps allowing to secure, to the ear of an animal, an identification device bearing visual and/or electronic identification information relating to this animal. It also relates to the field of clamps allowing to handle a device for sampling an animal tissue.

More specifically, the invention relates to the manner for holding secured to the jaws of the clamp the elements that compose such an identification and/or tissue sampling device.

2. PRIOR ART

In order to ensure animal identification in particular to meet sanitary and traceability requirements, identification devices are placed on farm animals in particular pigs, cattle, sheep/goats or others.

Among these identification devices, mention may be made to earrings.

Conventionally, these earrings comprise a female element and a male element intended to be placed on either side of an ear and to cooperate together to hold the earring secured to the ear.

As represented in FIGS. 1a and 1b, respectively illustrating a front view and a side view of an example of a female element, such an element 1 herein comprises an information carrier plate 10 prolonged at one of its end by a locking housing 11 closed by a cap 110.

As represented in FIGS. 2a and 2b, respectively illustrating a front view and a side view of an example of a male element, such an element 2 herein comprises a plate 20 prolonged at one of its ends by a locking tip 21 intended to cooperate with the locking housing 11 of the female element 1.

At least one, or both, of the female and male elements may carry information enabling in particular the identification of the animal. For example, this information may consist of visually legible markings (alphanumeric markings, barcode . . . ) and/or of information recorded on an electronic medium such as an RFID tag or others.

The set-up of such an earring implies the use of a clamp designed to this end as illustrated in FIG. 3.

A clamp 3 of this type comprises a handle 31 comprising two arms 310, 311 hinged to one another and each prolonged by a jaw 33, 32 respectively.

The jaw 33 carries a punch 34 along which a male element 2 can be forcibly fitted by inserting the punch 34 into a housing with a complementary shape 210 formed inside the locking tip 21.

The jaw 32 comprises a receptacle 320 suitable for housing the cap 110 of a female element 1. It also carries a flange 321 (also called pedal) intended to hold a female element 1 secured to the jaw 32.

This flange 321 comprises a fork-like shaped end 3210 with a front opening enabling the passage of the locking tip 21 of a male element 2. It extends towards the joint area of the arms 310, 311 by an actuation tab 3211 on which an operator can act to bring the fork 3210 away from or close to the end of the jaw 32, a spring tending to bring the fork 3210 close to the end of the jaw 32.

The set-up of such an identification earring on the ear of an animal is achieved in the following way.

An operator seizes with his first hand the handle 31, then fits with his second hand a male element 2 along the punch 34. Afterwards, he seizes a female element 1 in his second hand and brings it close to the jaw 32 in order to insert the cap 110 into the receptacle 320. For this purpose, he displaces his first hand so as to seize the clamp no longer by the handle 31 but at the jaw 32 so as to be able to act on the actuation tab 3211 to raise the fork 3210 with his first hand and thus clear access to the receptacle 320. The operator can then position the female element 1 with his second hand between the jaw 32 and the flange 321 by inserting the cap 110 into the housing 320. Finally, the operator releases the actuation tab 3211 such that the flange 321 gets close to the jaw 32 by the effect of the spring to hold the female element 1 secured to the jaw 32.

Afterwards, the operator places an ear 0 between the two jaws 32, 33, then actuates the handle 31 to bring the jaws close to one another until the locking tip 21 fits into the locking housing 11.

Thus, the female element 1 and the male element 2 grip the ear 0 such that the earring is irreversibly secured therein, as represented in FIG. 4.

Although effective and relatively simple to implement, this technique may nevertheless be improved even more.

Indeed, it is not always obvious for the operator to hold the clamp and handle the flange 321 with one hand and handle the female element 1 with the other hand. For this purpose, in general, the operator seizes the clamp with one hand, not by the handle 31 but in the region of the joint of the two arms 310, 311, so as to be able to hold the clamp and handle the actuation tab 3211 of the flange 321 with the same hand and handle the female element 1 with the other hand. Nonetheless, this practice is not optimal to the extent that the operator does not then hold the clamp comfortably by its handle 31, which has a negative impact on productivity. Hence, there is a need to improve in particular the ergonomics of clamps enabling the set-up of identification earrings. This need also exists for clamps enabling handling a device for sampling an animal tissue, such a device comprising a sampling tube (receptacle) having to be reversibly secured to one of the jaws of the clamp during sampling.

3. OBJECTIVES OF THE INVENTION

In particular, it is an objective of the invention to provide an effective solution to at least some of these different problems.

In particular, according to at least one embodiment, it is an objective of the invention to provide a clamp for handling a device for identifying an animal and/or sampling an animal tissue which allows to facilitate the work of an operator performing this task, and in particular to improve ergonomics.

In particular, it is an objective of the invention, according to at least one embodiment, to provide such a clamp which enables the operator to comfortably hold the clamp by its handle throughout the set-up of an identification earring on the ear of an animal, and in particular during the set-up of the male and/or female elements on the clamp, or the completion of a tissues sampling.

It is another objective of the invention, according to at least one embodiment, to provide such a clamp that has a simple and/or robust and/or economical design and/or whose use contributes to improving productivity.

4. DISCLOSURE OF THE INVENTION

For this purpose, the invention provides Clamp for handling a device for identifying an animal and/or sampling animal tissue, said clamp comprising two jaws, a handle for moving said jaws together, and means for securing an element of said identification and/or sampling device to one of said jaws, said securing means being movable between:
- a release position wherein they do not secure said element of said identification and/or sampling device to said jaw, and
- a securing position wherein they secure said element of said identification and/or sampling device to said jaw.

According to the invention, said clamp comprises actuation means for moving said securing means from one to the other position thereof, said actuation means being actuatable via said handle.

Thus, according to this aspect of the invention, an operator can comfortably grip the handle and act on the actuation means with the same hand to achieve securing of one of the elements of an identification earring. Thus, he can set the element of the identification earring in place with the other hand to secure it in the clamp. In the case of a sampling device, the operator can thus comfortably handle the clamp with one hand while he brings the sampling tube close with the other hand to hold it secured to the clamp.

Thus, the ergonomics are improved by enabling the operator to handle the clamp comfortably with one hand and handle the portions of the earring or of the sampling tube with the other hand.

Thus, the technique according to the invention allows go improve comfort of the operator and to improve productivity by helping him save time.

According to a possible variant, said identification device comprises a female element and a male element intended to be placed on either side of an animal's ear and to be moved together to engage with one another and secure said identification device to said ear, said female and male elements being each intended to be supported by one of said jaws, said securing means being movable between:
- a release position wherein said securing means are moved away from said corresponding jaw, and
- a securing position wherein said securing means are moved towards said corresponding jaw to secure if necessary said male element or said female element between said securing means and said corresponding jaw.

In this case, an element of an identification device may be effectively secured between the securing means and the corresponding jaw.

According to a possible variant, said securing means are movably mounted about a first axis of rotation between the securing position thereof and the release position thereof.

According to a possible variant, said securing means are movably mounted along an axis of translation between the securing position thereof and the release position thereof.

According to a possible variant, said handle comprises two arms rotatably mounted along a second axis of rotation, said first axis of rotation (Z) being essentially parallel with said second axis of rotation or said axis of translation (B) being essentially orthogonal to said second axis of rotation.

In some variants, the axis of rotation of the securing means may be coincident with that of the arms or the axis of translation of the securing means may be secant to the axis of rotation of the branches. The axis of rotation of the securing means may be coincident with that of the arms or the axis of translation of the securing means may also be remote from the axis of rotation of the arms.

A clamp according to the invention may comprise elastic return means tending to return said securing means to one position thereof, the actuation means being used to move same to the other position thereof.

According to a possible variant, said securing means comprise a flange movable between:
- said release position wherein said flange and said corresponding jaw are moved apart to release said male element or said female element, and
- a securing position wherein said flange and said corresponding jaw are moved together to grip said male element or said female element between said flange and said corresponding jaw.

According to a possible variant, said actuation means comprise at least one lever extending to the end of said handle situated on the side of said jaws so as to be suitable for being actuated by a finger of a hand grasping said handle.

This allows to improve ergonomics.

According to a possible variant, said at least one lever is connected to a flank to which said flange is connected.

According to a possible variant, said lever forms with said flank and said flange a one-piece assembly.

According to a possible variant, said flank bears at least two slots stretching along a same circle wherein the centre passes via the first axis of rotation of the securing means, said slots housing mounting axis for engaging said flank with the rest of said clamp.

According to a possible variant, said flank bears at least two oblong slots stretching along said axis of translation of the securing means, said oblong slots housing mounting axis for engaging said flank with the rest of said clamp.

According to a possible variant, said slots or said oblong slots are laterally offset from said first axis of rotation towards said handle.

This allows to clear more space between the jaws to accommodate an ear therein.

According to a possible variant, said sampling device comprises a receptacle suitable for receiving a sample, said securing means comprising two grips placed facing one another movably mounted between:
- a release position wherein said grips are moved apart to release said receptacle, and
- a securing position wherein said grips are moved together to secure said receptacle to said corresponding jaw.

According to at least one embodiment, the securing means comprise at least one securing element (for example a flange or a pair of grips) movable between:
- a release position in which it does not hold said element of said identification and/or sampling device secured to said jaw, and
- a securing position in which it holds said element of said identification and/or sampling device secured to said jaw by gripping.

According to this embodiment, said clamp comprises actuation means to displace said at least one securing element from one to the other position thereof, said actuation means comprising at least one actuation element (for example a lever or a button) that can be manually actuated from the handle by means of a hand gripping the handle.

5. LIST OF FIGURES

Other features and advantages of the invention will appear on reading the following description of particular embodiments, provided simply as illustrative and non-limiting examples, and from the appended drawings amongst which:

FIGS. 1a and 1b illustrate front and side views of a female element of an identification earring;

FIGS. 2a and 2b illustrate front and side views of a male element of an identification earring;

FIG. 3 illustrates a clamp according to the prior art for the set-up of an identification earring;

FIG. 4 illustrates securing of an identification earring to the ear of an animal;

6. DESCRIPTION OF PARTICULAR EMBODIMENTS

6.1. Architecture of a Clamp

Figure 5:
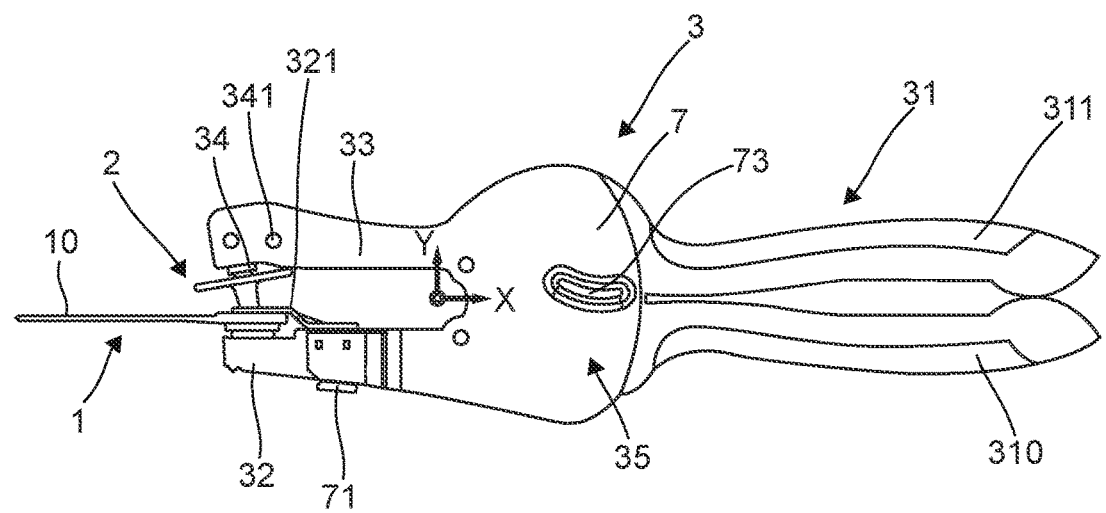
FIG. 5 illustrates a side view of a clamp according to the invention, in the closed position, on which an identification earring is set in place, and whose securing means are in the securing position.
Figure 6:
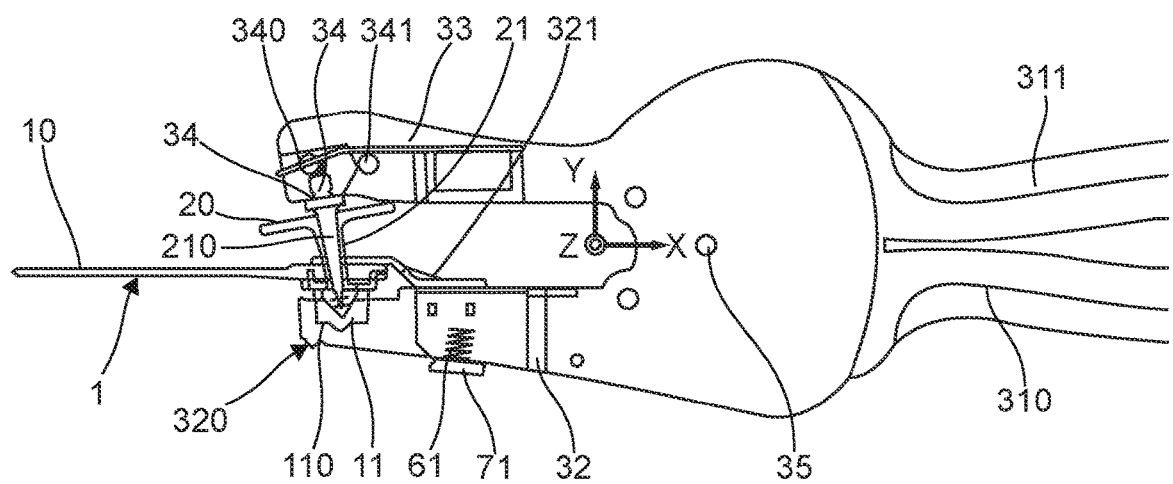
FIG. 6 illustrates a partial longitudinal sectional view of the clamp of FIG. 5.
Figure 7:
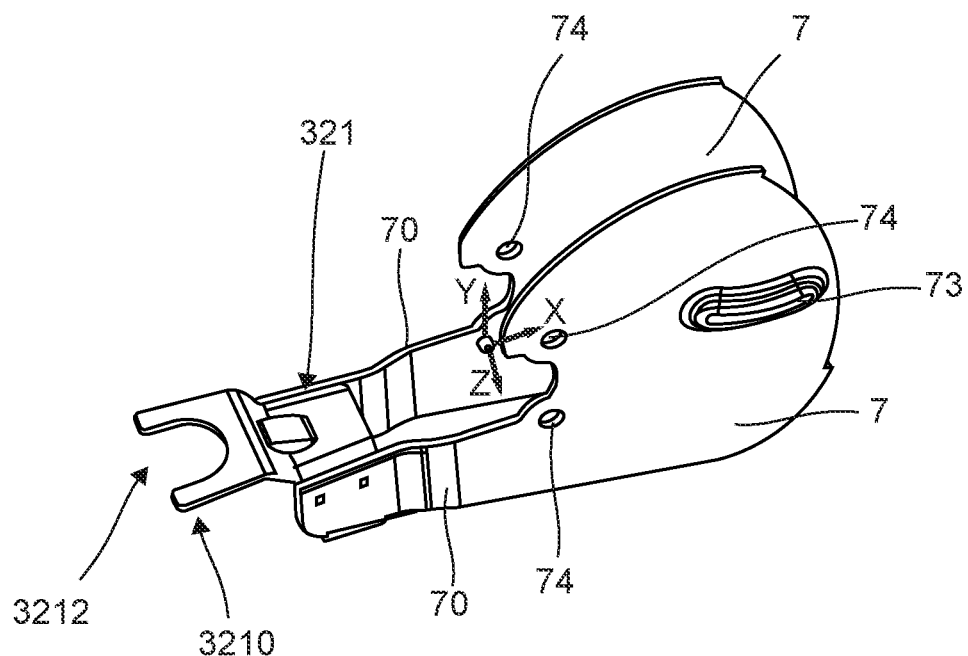
FIGS. 7 and 8 illustrate perspective views of a clamp according to the invention.
Figure 8:
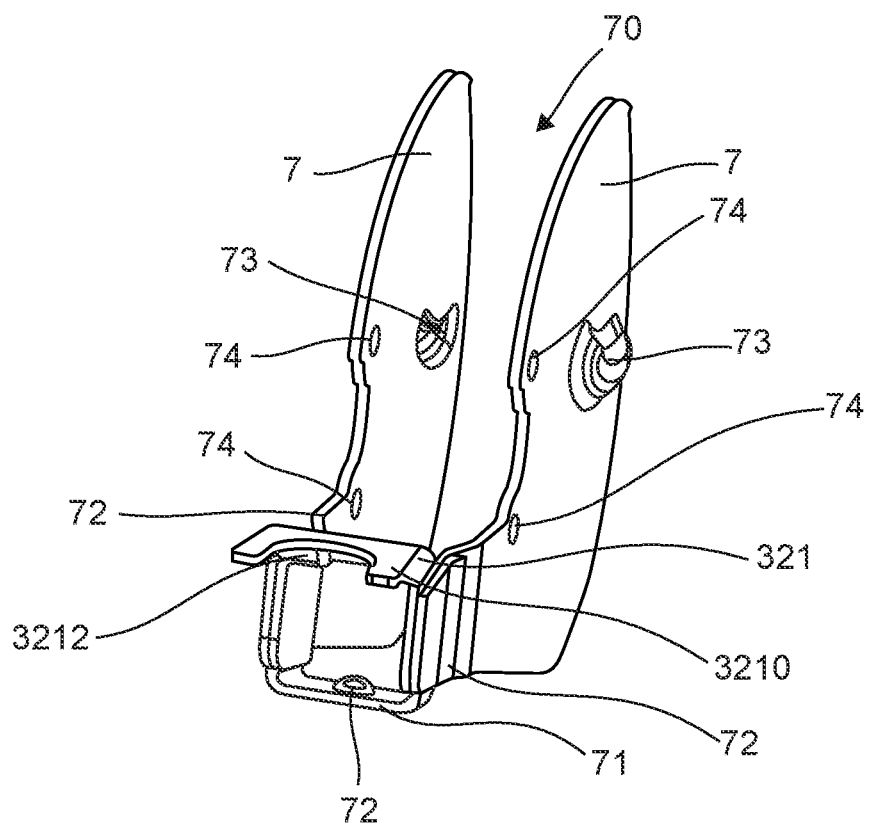

An embodiment of a clamp according to the invention for the set-up of an identification earring on the ear of an animal is presented with reference to FIGS. 5 to 12.

Conventionally, such a clamp 3 comprises a handle 31 comprising two arms 310, 311 each prolonged by a jaw 32, 33.

Conventionally, the two arms 310, 311 are linked by a joint 35 comprising a pivot connection such that bringing the arms 310, 311 close to one another by displacing one of them relative to the other according to the axis of this pivot connection is accompanied by bringing the jaws 32, 33 together, and vice versa.

The jaw 32 carries a punch 34 along which a male element 2 can be forcibly fitted by inserting the punch 34 into a housing with a complementary shape 210 formed inside the locking tip 21.

In this embodiment, the punch 34 is mounted on a support 340 movably mounted in the jaw 33 according to the axis 341 of a pivot connection essentially parallel to the axis of the joint 35 of the arms 310, 311. In one variant, the pivot 34 may be fixed relative to the jaw 33 to which it is secured.

The jaw 32 comprises a receptacle 320 suitable for housing the cap 110 of a female element 1. It also carries a flange 321 (also called pedal) intended to hold a female element 1 secured to the jaw 32.

This flange 321 comprises a fork-like shaped end 3210 with a front opening 3212.

The flange 320 is secured, at its end opposite to that of the fork 3210, to two flanks 7 essentially parallel and distant from one another to form an internal space 70.

Each of these two flanks 7 is prolonged by an extension 72 at the end of which they are linked by a bridge 71. A boss 72 is formed on the bridge 71.

An actuation lever 73 is formed at the surface of each flank 7. In this instance, more particularly, it consists of an actuation boss. Implementing an actuation boss 73 on each flank enables actuation by a right-handed as well as by a left-handed or actuation by two different fingers (for example the thumb and the index). In another variant, one single flank may be implemented. The surface of the actuation bosses 73 intended to be in contact with a finger may be curved to substantially conform to the shape of the finger and thus improve ergonomics.

The internal space 70 is intended to house the rest of said clamp 1 at the joint 35 of the arms 310, 311.

The two flanks 7, the extensions 72 and the bridge 71 are formed from a stamped and folded sheet metal to which the flange 320 is secured by crimping at the end of the extensions 72 to form a one-piece assembly. A fastening means other than crimping, such as welding, screwing, gluing or others may be implemented to ensure securing of the flange. In one variant, the flange may also be formed from the sheet metal of the flanks and folded.

Each flank 7 is crossed by two slots 74 (it is nonetheless possible to implement only one). These slots 74 are oblong and stretch along a circle C with a centre A. They are essentially shaped like a ring portion (crescent portion). They house axes 75 for securing the flanks 7 to the rest of the clamp 1.

Thus, the flange 320 is mounted movable in rotation about a first axis of rotation 2 passing via the centre A of the circle C and essentially parallel with the axis of the pivot connection 35 of the joint of the arms 310, 311.

In this case, the axes of rotation of the flange 320 and of the arms 310, 311 are different. Nonetheless, they may be coincident.

The oblong slots 74 are laterally offset from the first axis of rotation Z towards the handle 31, which allows clearing more space between the jaws 32, 33 to accommodate an ear therein.

Thus, the flange 321 is movable between:
a release position in which the flange 320 and the jaw 32 are moved apart to release the female element placed therebetween, and
a securing position in which the clamp 320 and the jaw 32 are moved together to hold the female element gripped between the flange and the jaw 32.

A compression spring 61 placed on the boss 73 between the bridge 71 and the jaw 32 tends to return the flange 320 back to its securing position.

An operator can act on the actuation bosses 73 to modify the position of the flange 320.

The actuation bosses 73 are placed such that when an operator grips the handle 31 with one hand, these actuation bosses "fall" beneath a finger of this hand, in particular the thumb or the index. Thus, the actuation bosses 73 can be actuated by one finger of the hand gripping the handle 31.

Figure 13:
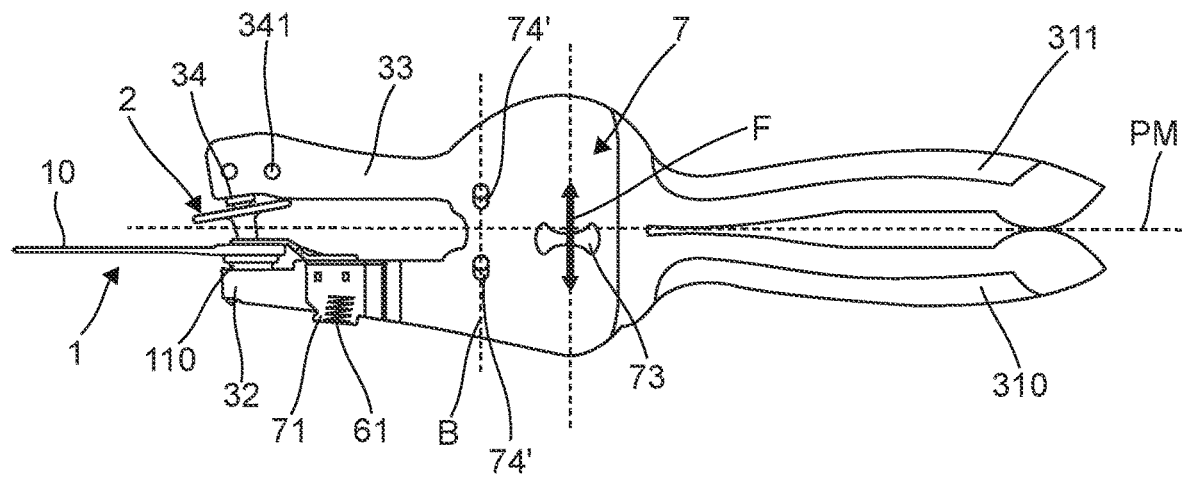
FIGS. 13 and 14 illustrate side views of a clamp in the closed position with securing means displaceable in translation respectively in the securing position and in the release position.
Figure 14:
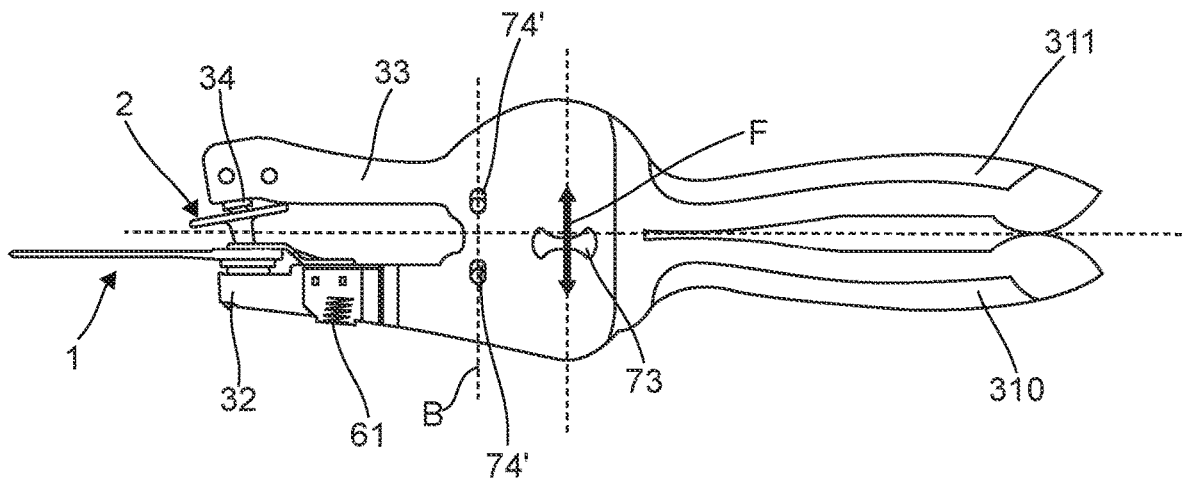
Figure 15:
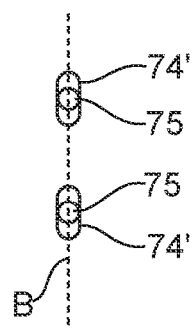
FIG. 15 illustrates a detail of the oblong slots of the clamp illustrated in FIGS. 13 and 14.

In one variant, illustrated in FIGS. 13 to 15, the flange 320 is movably mounted between its positioned along an axis of translation B essentially orthogonal to a midplane PM of the clamp extending between its jaws and its arms when the clamp is closed and passing via the axis of rotation of the joint 35 of the arms 32, 33.

In this case, the oblong slots 74' stretch according to this axis of translation B.

Of course, the axis of translation may be directed differently (for example it may be inclined with respect to the midplane PM, or else extend in this plane—in this case the displacement of the flange from one to the other position thereof may be done by sliding from the right to the left in the figures—, and orthogonal to the axis of the joint of the arms) provided that it will allow to carry out a displacement of the flange from one to the other position thereof. In the case of a sliding in the plane PM or in a plane essentially parallel therewith, indicating that in the release position, the securing means are away from the corresponding jaw, and that in the securing position, they are close to the corresponding jaw, means that they are brought respectively close to or away from the end of the jaw.

6.2. Operation of a Clamp

The set-up of an identification earring on the ear of an animal is achieved in the following way.

An operator seizes with his first hand the handle 31, then fits with his second hand a male element 2 along the punch 34.

The flange 321 lies in its securing position in which it is secured by the effect of the spring 61. The flange 320 is then brought close to the jaw 32.

Figure 9:
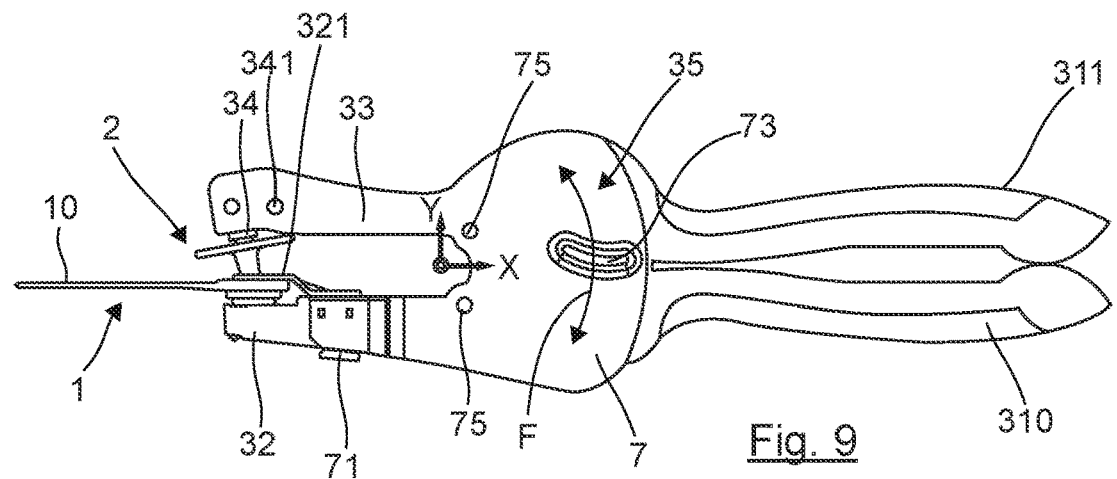
FIG. 9 illustrates a side view of a clamp according to the invention in the closed position, in which an identification earring is set in place, with the flange in the release position.
Figure 11:
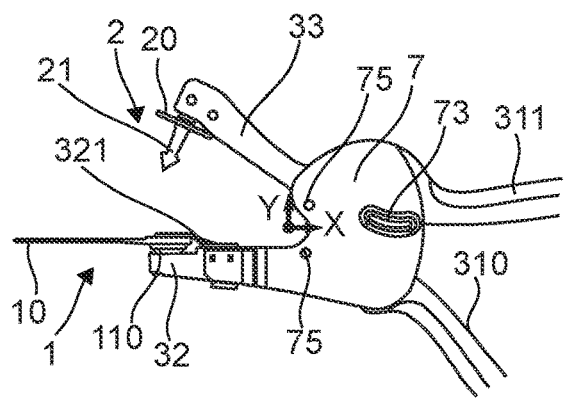
FIG. 11 illustrates a side view of a clamp according to the invention in the open position, on which an identification earring is set in place, with the clamp in the securing position.
Figure 10:
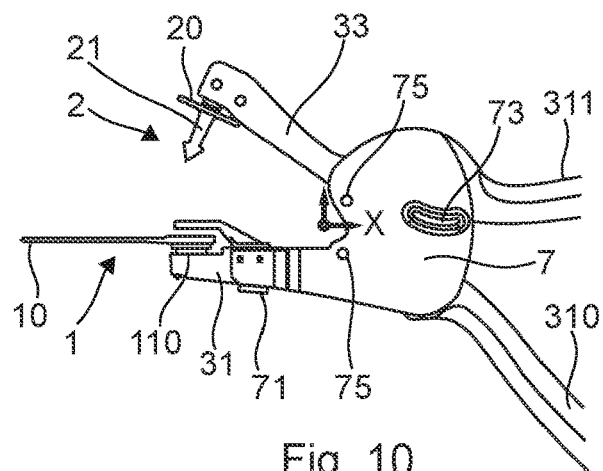
FIG. 10 illustrates a side view of a clamp according to the invention in the open position, on which an identification earring is set in place, with the flange in the release position.
Figure 12:
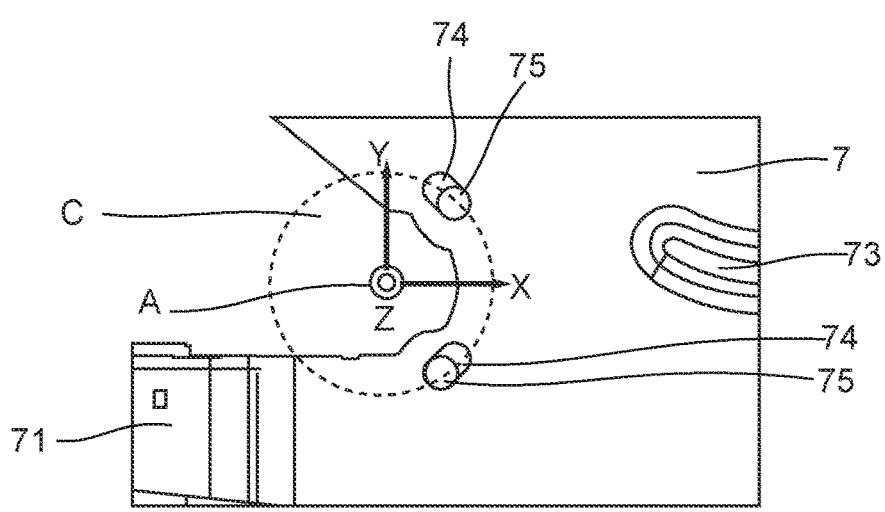
FIG. 12 illustrates a detail view of FIGS. 10 and 11.

Afterwards, the operator acts on an actuation boss 73 with a finger of the hand with which he comfortably grips the handle 31 so as to place the flange 321 in its release position in which it is moved apart from the jaw 32 through a rotational or translational movement (cf. the arrows F in FIGS. 9 and 13). Access to the housing 320 is then cleared.

Afterwards, the operator seizes a female element 1 in his second hand, brings it close to the jaw 32 and then positions the female element 1 between the jaw 32 and the flange 321 by inserting the cap 110 into the housing 320 with this hand.

The operator releases the actuation boss 73 such that the flange 321 returns back in its securing position by the effect of the spring 61. The female element 1 is then gripped between the flange and the jaw 32 and is thus secured in position.

Afterwards, the operator places an ear 0 between the two jaws 32, 33, then actuates the handle 31 to bring the jaws close to one another until the locking tip 21 fits into the locking housing 11.

Thus, the female element 1 and the male element 2 grip the ear 0 such that the earring is irreversibly secured therein, as represented in FIG. 4.

Afterwards, the operator releases the handle 31 to open the clamp and then clear it from the animal.

A system for automatically opening the clamp may also be provided. At the end of the closure stroke of the arms 310, 311, such a system allows to obtain a reopening of the jaws 32, 33 without opening the arms 310, 311.

6.3. Variants

In the above-described embodiment, the elastic return means tend to return the flange to its securing position and the actuation means are actuated to place them in their release position. This operation may be reversed.

Figure 16:
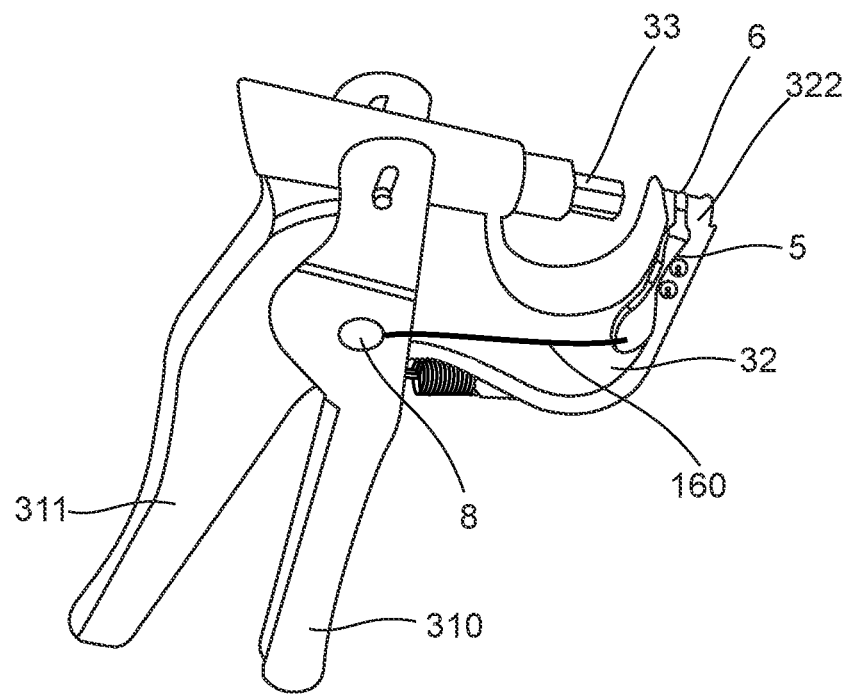
FIGS. 16 and 17 illustrate a variant of a clamp for handling a tissue sampling device.
Figure 17:
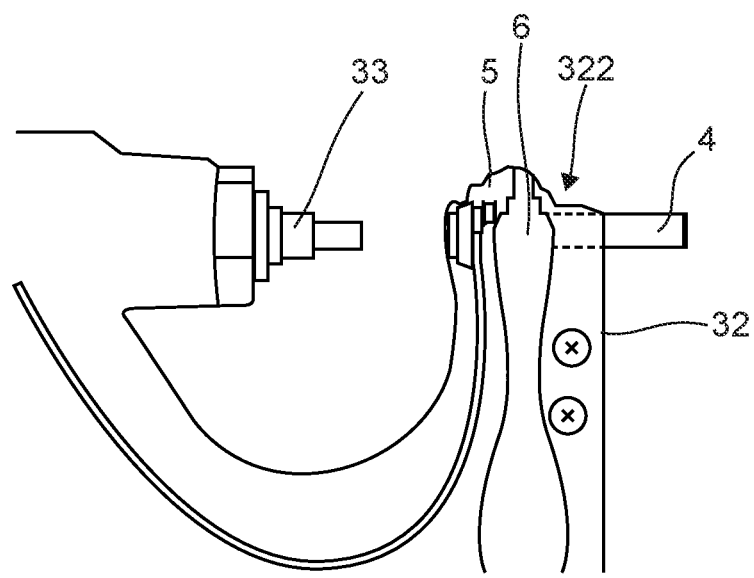

The implementation of securing means with a remote control has just been described in the context of a clamp for handling a device for identifying an animal. Nonetheless, such securing means with a remote control may also be implemented in the context of a clamp for handling a device for sampling a tissue of an animal such that illustrated in FIGS. 16 and 17.

In this case, one of the jaws, in this case the jaw 32, is fixed whereas the other jaw 33 is movable so as to be brought close to or away from the jaw 32.

The jaw 32 has an end lateral opening 322 into which a sampling tube 4 (receptacle) can be laterally inserted.

In this instance, the jaw 33 is a piston which allows cutting and pushing a tissue of an animal in the sampling tube 4.

The sampling tube 4 may be held secured to the jaw 32 by means of a pair of grips 5, 6 placed facing one another on either side of the opening 322.

These grips 5, 6 are movably mounted between:
  a release position in which their free ends are moved apart from one another to clear the opening 322 and thus enable the lateral introduction of a sampling tube 4 into the latter or else extract a sampling tube 4 from the latter;
  a securing position in which their free ends are moved together to close the opening 322 and thus keep a sampling tube 4 gripped therein.

An actuation button 8, shifted at the end of the arms 310, 311 allows to actuate the grips 5, 6 remotely to make them move from one to the other position thereof.

This actuation button 8 is linked to the grips 5, 6 by means of a transmission 160 so that the actuation of the button 8 allows to displace the grips 5, 6 from one to the other position thereof. For example, it may consist of a flexible and/or rigid transmission. For example, it may consist of a transmission with one or more rod(s), cable(s), etc.

To perform a sampling, an operator seizes the clamp with one hand and, while the jaws 32, 33 are away from one another, he acts on the actuation button 8 to place the grips 5, 6 in their release position. Then, he can position with the other hand a sampling tube 4 in the lateral opening 322 and hold it therein and then acts on the actuation button 8 with the other hand to place the grips 5, 6 in their securing position. Afterwards, the operator can place a portion of an animal, such as an ear, between the jaws 32, 33. Afterwards, he actuates the arms 310, 311 so as to bring the jaws 32, 33 close to one another. The jaw 33 then cuts a piece of the ear and pushes it in the sampling tube 4. Afterwards, the operator releases the clamp to bring the jaws away from one another and clear the clamp from the animal and then acts on the actuation button 8 to place the grips 5, 6 in their release position and thus recover the sampling tube 4.

In one variant, the actuation button 8 will enable an operator to place the grips 5, 6 in their securing position against the effect of elastic return means. In this case, releasing the actuation button 8 will enable the grips 5, 6 to return back to their release position by the effect of the elastic return means. This operation may be reversed.

Some sampling devices also enable the placement of an identification device.

The invention claimed is:

1. A Clamp for handling an identification device for identifying an animal, said clamp comprising two jaws;
  a handle comprising two arms linked by a joint for moving said two jaws together and;
  securing means for securing an element of said identification device to one of said two jaws;
  said securing means comprising
    a flange,
    at least one flank connected to the flange, said at least one flank extending to the joint, and at least one actuation means connected to the at least one flank said securing means being movable between at least two positions:

a release position wherein said securing means does not secure said element of said identification device to the one of said two jaws, and a securing position wherein said securing means holds said element of said identification device secured to the one of said two jaws by gripping, characterized in that said actuation means actuates said securing means from one of said at least two positions to the other position, said at least one actuation means being manually actuatable by means of a hand gripping one of the arms of the handle.

2. The Clamp according to claim 1, wherein said securing means are movable between:

said release position wherein said securing means are moved away from a corresponding jaw, and said securing position wherein said securing means are moved towards said corresponding jaw.

3. The Clamp according to claim 2, wherein said securing means comprise the flange movable between:

said release position wherein said flange and the corresponding jaw are moved apart to release a male element or a female element, and said a securing position wherein said flange and said corresponding jaw are moved together to grip said male element or said female element between said flange and said corresponding jaw.

4. The Clamp according to claim 1, wherein said at least one actuation means comprise at least one lever extending to an end of said handle situated on a side of said two jaws so as to be suitable for being actuated by a finger of said hand gripping one of the arms of said handle, said at least one lever is-being connected to the at least one flank to which said flange is connected.

5. The Clamp according to claim 1, wherein said securing means are movably mounted about a first axis of rotation between the securing position thereof and the release position thereof.

6. The Clamp according to claim 5, wherein said two arms of said handle are rotatably mounted along a second axis of rotation, said first axis of rotation being essentially parallel with said second axis of rotation.

7. The Clamp according to claim 5, wherein said at least one flank includes at least two slots stretching along a circle wherein a center of said circle lies on the first axis of rotation of the securing means.

8. The Clamp according to claim 7, wherein said slots are laterally offset from said first axis of rotation towards said handle.

9. The Clamp according to claim 1, wherein said securing means are movably mounted along an axis of translation between the securing position thereof and the release position thereof.

10. The Clamp according to claim 5 wherein said at least one flank bears at least two oblong slots stretching along said axis of translation of the securing means.

11. The Clamp according to claim 10, wherein said oblong slots are laterally offset from said first axis of rotation towards said handle.

12. The Clamp according to claim 1, comprising elastic return means configured to return said securing means to one of said at least two positions, the at least one of actuation means configured to move said securing means to the other of said at least two positions.

13. The Clamp according to claim 1, wherein said at least one actuation means comprise at least one lever.

14. The Clamp according to claim 13, wherein said lever is suitable for being actuated by a finger of said hand gripping at least one of the arms of said handle.

15. The Clamp according to claim 1, wherein said securing means is a one-piece assembly.

16. The Clamp according to claim 5, wherein said securing means comprises a one-piece assembly, and said at least one flank includes at least two slots stretching along a circle wherein a center of said circle lies on said first axis of rotation.

17. The Clamp according to claim 16, wherein said slots are laterally offset from said first axis of rotation towards said handle.

18. The Clamp according to claim 1, wherein the at least one actuation means is suitable for being actuated by a finger of said hand gripping at least one of the arms of said handle.

* * * * *